（12） United States Patent
Gaballa

(10) Patent No.: US 9,687,512 B2
(45) Date of Patent: Jun. 27, 2017

(54) ISOLATED CARDIAC STEM CELLS AND METHODS OF THEIR USE

(71) Applicant: Banner Health, Phoenix, AZ (US)

(72) Inventor: Mohamed A. Gaballa, Peoria, AZ (US)

(73) Assignee: Banner Health, Phoenix, AZ (US)

( * ) Notice: Subject to any disclaimer, the term of this patent is extended or adjusted under 35 U.S.C. 154(b) by 0 days.

(21) Appl. No.: 14/645,420

(22) Filed: Mar. 12, 2015

(65) Prior Publication Data

US 2015/0258147 A1 Sep. 17, 2015

Related U.S. Application Data

(60) Provisional application No. 61/951,538, filed on Mar. 12, 2014.

(51) Int. Cl.
*A61K 35/34* (2015.01)
*C12N 5/0775* (2010.01)
*A61K 45/06* (2006.01)
*G01N 33/569* (2006.01)

(52) U.S. Cl.
CPC .............. *A61K 35/34* (2013.01); *A61K 45/06* (2013.01); *C12N 5/0668* (2013.01); *G01N 33/56966* (2013.01); *G01N 2333/4703* (2013.01); *G01N 2333/4739* (2013.01); *G01N 2333/7055* (2013.01); *G01N 2333/70503* (2013.01); *G01N 2333/70539* (2013.01); *G01N 2333/70596* (2013.01); *G01N 2333/71* (2013.01); *G01N 2333/78* (2013.01); *G01N 2333/916* (2013.01); *G01N 2800/325* (2013.01)

(58) Field of Classification Search
CPC ................. A61K 35/34; C12N 5/0668; G01N 2800/325; G01N 2800/324
See application file for complete search history.

(56) References Cited

U.S. PATENT DOCUMENTS

2011/0123500 A1* 5/2011 Anversa ................ A61K 35/34
424/93.7
2015/0368618 A1* 12/2015 Nadal-Ginard ...... C12N 5/0607
424/93.7

OTHER PUBLICATIONS

Beltrami et al., Cell. Sep. 19, 2003;114(6):763-776.*
Li et al., Stem Cells, Nov. 2010;28(11):2088-2098.*

* cited by examiner

*Primary Examiner* — Daniel C Gamett
(74) *Attorney, Agent, or Firm* — Law Offices of Christopher Jacob, P.C.

(57) ABSTRACT

The present invention relates to isolated populations of cardiac stem cells. The invention provides methods for characterizing, isolating, and culturing cardiac stem cells from human tissue samples. The invention also provides compositions and methods useful for treating cardiac disease.

19 Claims, No Drawings

ISOLATED CARDIAC STEM CELLS AND METHODS OF THEIR USE

RELATED APPLICATIONS

This application claims priority to U.S. Provisional Patent Application Ser. No. 61/951,538, filed on Mar. 12, 2014, which is hereby incorporated by reference herein in its entirety.

STATEMENT OF RIGHTS UNDER FEDERALLY-SPONSORED RESEARCH

This invention was made with government support under NIH RO1 AG027263, awarded by the National Institute of Aging. The government has certain rights in this invention.

FIELD OF THE INVENTION

The present invention relates to isolated populations of cardiac stem cells. The invention provides methods for characterizing, isolating, and culturing cardiac stem cells from human tissue samples. The invention also provides compositions and methods useful for treating cardiac disease.

BACKGROUND OF THE INVENTION

More than 5.8 million Americans have heart failure (e.g., congestive heart failure). Heart failure is a complex clinical syndrome which results from structural and functional disorders of the heart associated with a variety of cardiovascular diseases. Heart failure is mainly characterized by a condition in which the heart cannot pump enough blood to the rest of the body. Although various therapies for heart failure may be used to manage the disease, heart failure has no cure.

The main limitations of current pharmacological, interventional, and operative therapies is their inability to compensate the irreversible loss of functional cardiomyocytes. Stem cell based therapies address this limitation by providing a means for the regeneration of cardiomyocytes and/or myocardial tissue to restore cardiac function.

Accordingly, there is a need in the art for isolated cardiac stem cells and methods for isolating cardiac stem cells. Additionally, there is a need in the art for stem cells and methods useful for treating heart failure and other cardiac diseases. The present invention meets this need by providing isolated cardiac stem cells. The present invention further provides cells and methods useful for treating heart failure and other cardiac diseases.

SUMMARY OF THE INVENTION

The present invention provides isolated populations of cardiac stem cells. The invention further provides methods for characterizing, isolating, and culturing stem cells from human tissue samples. The invention also provides compositions and methods useful for treating subjects with disease such as, for example, heart disease.

In some embodiments, the invention provides a composition comprising one or more isolated cardiac stem cells derived from non-embryonic tissue. In some embodiments, the cardiac stem cells express c-Kit, Nanog, and Sox2 but not CD34 or CD45. In certain embodiments, the tissue is human tissue. In yet other embodiments, the cardiac stem cells are human cardiac stem cells. In still other embodiments, the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, CD73, and Wt1. In other embodiments, the tissue is obtained from a subject having or suspected of having a cardiac disease. In some embodiments, the cardiac stem cells have an enhanced differentiation potential.

In some embodiments, the present invention provides methods for the isolation of cardiac stem cells, comprising the selective enrichment of cardiac stem cells which express c-Kit, Nanog, and Sox2 but not CD34 or CD45. In other embodiments, the methods further comprise dissociating a source of cardiac stem cells from a cardiac tissue sample; and identifying a cardiac stem cell expressing c-Kit, Nanog, and Sox2. In yet other embodiments, the methods further comprise centrifuging a suspension of cells from heart tissue of a subject on a density gradient; isolating a layer of cells comprising cardiac stem cells; culturing the isolated cells until a population of cardiac stem cells is detectable. In still other embodiments, the methods of the invention comprise obtaining heart tissue from a subject; digesting the heart tissue with collagenase. In some embodiments, the methods further comprise obtaining heart tissue from a subject having or suspected of having a cardiac disease. In other embodiments, the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, CD73, and Wt1.

In some embodiments, the present invention provides methods of treating a subject suffering from heart disease, comprising administering to the subject an effective dose of cardiac stem cells, wherein the cardiac stem cells express c-Kit, Nanog, and Sox2 but not CD34 or CD45. In some embodiments, the cardiac stem cells proliferate and differentiate to produce cardiomyocytes. In other embodiments, the subject has a heart disease selected from the group consisting of chronic heart failure, myocardial infarction, congestive heart failure, congenital heart disease, cardiomyopathy, pericarditis, angina, and coronary artery disease. In yet other embodiments, the methods further comprise administering an agent to the subject. In still other embodiments, the agent is selected from the group consisting of an ACE inhibitor, an aldosterone inhibitor, an angiotensin II receptor blocker, a beta-blocker, a calcium channel blocker, a statin, digoxin, a diuretic, a vasodilator, and an anticoagulant. In other embodiments, the methods further comprise administering an agent to the cardiac stem cells prior to administering the cardiac stem cells to the subject. In yet other embodiments, the agent is selected from the group consisting of PDGF, EGF, FGF, NGF, EPO, IGF-1, IGF-2, G-CSF, IL-6 INF, Stem Cell Factor, and TNF-α. In other embodiments, the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, CD73, and Wt1.

In some embodiments, the present invention provides a cardiac stem cell, wherein said stem cell is obtained from cardiac tissue, is isolated from an isolated cardiac cell cluster comprising cardiac stem cells, and wherein said cardiac stem cells express c-Kit, Nanog, and Sox2 but not CD34 or CD45. In some embodiments, the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, CD73, and Wt1.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the discovery of cardiac stem cells that may be isolated from human cardiac tissue. The present invention provides isolated cardiac stem cells. The invention also provides methods for characterizing, isolating, and culturing cardiac stem cells from human tissue samples. The invention further provides stem cells and methods useful for treating subjects with disease (e.g. heart disease).

The cardiac stem cells of the present invention have several applications in therapy and drug discovery. In therapeutic applications, the cells are administered to patients suffering from heart disease, such as, for example, necrotic cardiac tissue resulting from a myocardial infarction. The administered stem cells colonize the heart of a patient and give rise to myocardial progeny cells that replace necrotic cardiac tissue and/or supplement preexisting heart tissue.

In drug discovery applications, the cardiac stem cells of the present invention are used to screen compounds for activity in promoting or inhibiting differentiation of stem cells to cardiomyocytes or other mature differentiated cell types. Compounds that promote differentiation of stem cells to cardiomyocytes can be used for therapy of patients with heart disease, optionally in conjunction with the stem cells of the present invention. Other compounds can be used in other therapeutic applications in which promotion or inhibition of stem cell differentiation is desired. Yet another use for the cardiac stem cells of the present invention is screening for compounds which expand cardiac stem cell populations in culture. Still another therapeutic use for cardiac stem cells of the present invention is to provide a method to screen for compounds that promote mobilization of cardiac stem cells from the heart to the circulatory system.

In vivo assays for evaluating cardiac neogenesis include treating neonatal and mature animals with the cells of the present invention. The animals' cardiac function is measured as heart rate, blood pressure, LV pressure-rate production (tdp/dt) and cardiac output to determine left ventricular function. Post-mortem methods for assessing cardiac improvement include: increased cardiac weight, nuclei/cytoplasmic volume, staining of cardiac histology sections to determine proliferating cell nuclear antigen (PCNA) vs. cytoplasmic actin levels (Quaini et al. (1994) Circulation Res. 75: 1050-1063 and Reiss et al. (1996) Proc. Natl. Acad. Sci. 93: 8630-8635.) The cardiac stem cells of the present invention can be used in treatment of disorders associated with heart disease, i.e., myocardial infarction, coronary artery disease, congestive heart failure, hypertrophic cardiomyopathy, myocarditis, congenital heart defects and dilated cardiomyopathy. Stem cells of the present invention are useful for improving cardiac function, either by inducing cardiac myocyte neogenesis and/or hyperplasia, by inducing coronary collateral formation, or by inducing remodeling of necrotic myocardial area. Stem cells of the present invention are also useful for promoting angiogenesis and wound healing following angioplasty or endarterectomy, to develop coronary collateral circulation, for revascularization in the eye, for complications related to poor circulation such as diabetic foot ulcers, for stroke, following coronary reperfusion using pharmacologic methods and other indications where angiogenesis is of benefit.

The section headings are used herein for organizational purposes only, and are not to be construed as in any way limiting the subject matter described herein.

Stem Cells

Stem cells are undifferentiated cells defined by their ability at the single cell level to both self-renew and differentiate to produce progeny cells, including self-renewing progenitors, non-renewing progenitors, and terminally differentiated cells. Stem cells, depending on their level of differentiation, are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, which is able to give rise to all embryonic and extraembryonic cell types; (2) pluripotent, which is able to give rise to all embryonic cell types. i.e., endoderm, mesoderm, and ectoderm; (3) multipotent, which is able to give rise to a subset of cell lineages, but all within a particular tissue, organ, or physiological system (for example, hematopoietic stem cells (HSC) can produce progeny that include HSC (self-renewal), blood cell restricted oligopotent progenitors and the cell types and elements (e.g., platelets) that are normal components of the blood); (4) oligopotent, which is able to give rise to a more restricted subset of cell lineages than multipotent stem cells; and (5) unipotent, which is able to give rise to a single cell lineage (e.g., spermatogenic stem cells).

In one embodiment, the cardiac stem cells of the present invention are isolated. Most conventional methods to isolate a particular stem cell of interest involve positive and negative selection using markers of interest. Agents can be used to recognize cardiac stem cell markers, for instance labeled antibodies that recognize and bind to cell-surface markers or antigens on desired cardiac stem cells. Antibodies or similar agents specific for a given marker, or set of markers, can be used to separate and isolate the desired cardiac stem cells using fluorescent activated cell sorting (FACS), panning methods, magnetic particle selection, particle sorter selection and other methods known to persons skilled in the art, including density separation (Xu et al. (2002) Circ. Res. 91:501; U.S. patent application Ser. No. 20030022367) and separation based on other physical properties (Doevendans et al. (2000) J. Mol. Cell. Cardiol. 32:839-851). Alternatively, genetic selection methods can be used, where a cardiac stem cell can be genetically engineered to express a reporter protein operatively linked to a tissue-specific promoter and/or a specific gene promoter; therefore the expression of the reporter can be used for positive selection methods to isolate and enrich the desired cardiac stem cell. For example, a fluorescent reporter protein can be expressed in the desired cardiac stem cell by genetic engineering methods to operatively link the marker protein to a promoter active in a desired stem cell (Klug et al. (1996) J. Clin. Invest. 98:216-224; U.S. Pat. No. 6,737,054). Other means of positive selection include drug selection, for instance as described by Klug et al., supra, involving enrichment of desired cells by density gradient centrifugation. Negative selection can be performed, selecting and removing cells with undesired markers or characteristics, for example fibroblast markers, epithelial cell markers etc.

Cardiac stem cells of the present invention express genes that can be used as markers to detect the presence of cardiac stem cells. The polypeptide products of such genes can be used as markers for positive or negative selection. For example, cardiac stem cells of the present invention may express one or more of the following cell surface markers: c-Kit, Nanog, Sox2, Hey1, SMA, Vimentin, Cyclin D2, Snail, E-cadherin, Nkx2.5, GATA4, MHCa, TnT, KDR, CD105, CD90, CD29, CD73, and Wt1. Antibodies to these markers may be used to identify stem cells in a tissue sample.

In one embodiment, the methods provide for enrichment and isolation of stem cells. The stem cells are selected for a characteristic of interest. In some embodiments, a wide range of markers may be used for selection. One of skill in the art will be able to select markers appropriate for the desired cell type. The characteristics of interest include expression of particular markers of interest, for example specific subpopulations of stem cells and stem cell progenitors will express specific markers. In some embodiments, stem cells of the present invention are selected using one or more markers selected from the list consisting of c-Kit, Nanog, Sox2, Hey1, SMA, Vimentin, Cyclin D2, Snail, E-cadherin, Nkx2.5, GATA4, MHCa, TnT, KDR, CD105, CD90, CD29, CD73, Wt1, CD34, and CD45.

In one embodiment, the stem cells are expanded. The cells are optionally collected, separated, and further expanded, generating larger populations of stem cells for use in making cells of a particular cell type or cells having an enhanced efficiency of homologous recombination.

Tissue Samples

In some embodiments, stem cells of the present invention are isolated from human tissues. Any bodily tissue may be used in the methods of the present invention, including, for example, tissue from an organ, from skin, from adipose, and from blood. Organ tissues useful for the compositions and methods of the present invention include heart or cardiac tissue. In certain embodiments, stem cells are isolated from heart tissue from atrial or ventricular biopsy specimens from human subjects. Such subjects may have heart disease selected from the group consisting of chronic heart failure, myocardial infarction, congestive heart failure, congenital heart disease, cardiomyopathy, pericarditis, angina, and coronary artery disease.

Isolation and Maintenance of Stem Cells

In some embodiments, stem cells are isolated from a sample or biopsy of bodily tissue by digested by enzymatic digestion, mechanical separation, filtration, centrifugation and combinations thereof. The number and quality of the isolated stem cells can vary depending, e.g., on the quality of the tissue used, the compositions of perfusion buffer solutions, and the type and concentration of enzyme. Frequently used enzymes include, but are not limited to, collagenase, pronase, trypsin, dispase, hyaluronidase, thermolysin and pancreatin, and combinations thereof. Collagenase is most commonly used, often prepared from bacteria (e.g. from *Clostridium histolyticum*), and may often consist of a poorly purified blend of enzymes, which may have inconsistent enzymatic action. Some of the enzymes exhibit protease activity, which may cause unwanted reactions affecting the quality and quantity of viable/healthy cells. It is understood by those of skill in the art to use enzymes of sufficient purity and quality to obtain viable stem cell populations.

The methods of the invention comprise culturing the stem cells obtained from human tissue samples. In one embodiment, the populations of stem cells are plated onto a substrate. In the present invention, cells (e.g., stem cells) are plated onto a substrate which allows for adherence of cells thereto, i.e., a surface which is not generally repulsive to cell adhesion or attachment. This may be carried out, e.g., by plating the cells in a culture system (e.g., a culture vessel) which displays one or more substrate surfaces compatible with cell adhesion. When the said one or more substrate surfaces contact the suspension of cells (e.g., suspension in a medium) introduced into the culture system, cell adhesion between the cells and the substrate surfaces may ensue. Accordingly, the term "plating onto a substrate which allows adherence of cells thereto" refers to introducing cells into a culture system which features at least one substrate surface that is generally compatible with adherence of cells thereto, such that the plated cells can contact the said substrate surface. General principles of maintaining adherent cell cultures are well-known in the art.

As appreciated by those skilled in the art, the cells may be counted in order to facilitate subsequent plating of the cells at a desired density. Where, as in the present invention, the cells after plating may primarily adhere to a substrate surface present in the culture system (e.g., in a culture vessel), the plating density may be expressed as number of cells plated per $mm^2$ or $cm^2$ of the said substrate surface.

Typically, after plating of the stem cells of the present invention, the cell suspension is left in contact with the adherent surface to allow for adherence of cells from the cell population to the said substrate. In contacting the stem cells with adherent substrate, the cells may be advantageously suspended in an environment comprising at least a medium, in the methods of the invention typically a liquid medium, which supports the survival and/or growth of the cells. The medium may be added to the system before, together with or after the introduction of the cells thereto. The medium may be fresh, i.e., not previously used for culturing of cells, or may comprise at least a portion which has been conditioned by prior culturing of cells therein, e.g., culturing of the cells which are being plated or antecedents thereof, or culturing of cells more distantly related to or unrelated to the cells being plated.

The medium may be a suitable culture medium as described elsewhere in this specification. Preferably, the composition of the medium may have the same features, may be the same or substantially the same as the composition of medium used in the ensuing steps of culturing the attached cells. Otherwise, the medium may be different.

Cells from the stem cell population or from tissue explants of the present invention, which have adhered to the said substrate, preferably in the said environment, are subsequently cultured for at least 7 days, for at least 8 days, or for at least 9 days, for at least 10 days, at least 11, or at least 12 days, at least 13 days or at least 14 days, for at least 15 days, for at least 16 days or for at least 17 days, or even for at least 18 days, for at least 19 days or at least 21 days or more. The term "culturing" is common in the art and broadly refers to maintenance and/or growth of cells and/or progeny thereof.

In some embodiments, the stem cells may be cultured for at least between about 10 days and about 40 days, for at least between about 15 days and about 35 days, for at least between about 15 days and 21 days, such as for at least about 15, 16, 17, 18, 19 or 21 days. In some embodiments, the stem cells of the invention may be cultured for no longer than 60 days, or no longer than 50 days, or no longer than 45 days.

The tissue explants and stem cells and the further adherent stem cells are cultured in the presence of a liquid culture medium. Typically, the medium will comprise a basal medium formulation as known in the art. Many basal media formulations can be used to culture the stem cells herein, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, and modifications and/or combinations thereof. Compositions of the above basal media are generally known in the art and it is within the skill of one in the art to modify or modulate concentrations of media and/or media supplements as necessary for the cells cultured. In some embodiments, a culture medium formulation may be explants medium (CEM) which is composed of IMDM supplemented with 10% fetal bovine serum (FBS, Lonza), 100 U/ml penicillin G, 100 µg/ml streptomycin and 2 mmol/L L-glutamine (Sigma-Aldrich). Other embodiments may employ further basal media formulations, such as chosen from the ones above.

For use in culture, media can be supplied with one or more further components. For example, additional supplements can be used to supply the cells with the necessary trace elements and substances for optimal growth and expansion. Such supplements include insulin, transferrin, selenium salts, and combinations thereof. These components can be included in a salt solution such as, but not limited to, Hanks' Balanced Salt Solution (HBSS), Earle's Salt Solution. Further antioxidant supplements may be added, e.g., β-mercaptoethanol. While many media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Also contemplated is supplementation of cell culture medium with mammalian plasma or sera. Plasma or sera often contain cellular factors and components that are necessary for viability and expansion. The use of suitable serum replacements is also contemplated (e.g., FBS).

As described, the present inventors have realized that by culturing tissue explants and stem cells for time durations as defined above, and preferably using media compositions as described above, a progenitor or stem cell of the invention emerges and proliferates. As detailed in the Examples section, the progenitor or stem cell may be distinguished from other cell types present in the primary cell culture by, among others, its expression of various markers.

Characterization of Stem Cells

In some embodiments, stem cells of the present invention are identified and characterized by their expression of specific marker proteins, such as cell-surface markers. Detection and isolation of these cells can be achieved, e.g., through flow cytometry, ELISA, and/or magnetic beads. Reverse-transcription polymerase chain reaction (RT-PCR) can also be used to monitor changes in gene expression in response to differentiation. Methods for characterizing cardiac stem cells of the present invention are provided herein. In certain embodiments, the marker proteins used to identify and characterize the stem cells are selected from the list consisting of c-Kit, Nanog, Sox2, Hey1, SMA, Vimentin, Cyclin D2, Snail, E-cadherin, Nkx2.5, GATA4, MHCa, TnT, KDR, CD105, CD90, CD29, CD73, Wt1, CD34, and CD45.

Differentiation Potential of Stem Cells

In some embodiments, the methods of the present invention enhance the differentiation potential of stem cells isolated from a human tissue. Differentiation potential can be assessed by culturing stem cells and subsequently measuring the expression levels of a pluripotency marker. In one embodiment, cardiac stem cells are cultured and the expression levels of cardiac troponin T (TnT) are measured by immunohistochemistry to determine differentiation potential.

Identification and subsequent isolation of differentiated cells from their undifferentiated counterparts can be carried out by methods well known in the art. For example, cells that have been induced to differentiate can be identified by selectively culturing cells under conditions whereby differentiated cells outnumber undifferentiated cells. Similarly, differentiated cells can be identified by their expression of specific marker proteins, such as cell-surface markers. Detection and isolation of these cells can be achieved, e.g., through flow cytometry, ELISA, and/or magnetic beads. Reverse-transcription polymerase chain reaction (RT-PCR) can also be used to monitor changes in gene expression in response to differentiation. In addition, whole genome analysis using microarray technology can be used to identify differentiated cells.

Subjects

In certain embodiments of all the above-described methods, the subject is a human subject. In certain embodiments, the subject is diagnosed with or suspected of having had a disease. In other embodiments, the patient is diagnosed with or suspected of having a heart disease, or is believed to have been exposed to or to be at risk for exposure to a heart disease. In some embodiments, the subject has a heart disease selected from the group consisting of chronic heart failure, myocardial infarction, congestive heart failure, congenital heart disease, cardiomyopathy, pericarditis, angina, and coronary artery disease.

Methods of Treatment

Heart disease may be treated by administration of cardiac stem cells of the present invention. The cells of the present invention can be administered either intravenously, intracoronary, or intraventricularly. A catheter can be used for the latter two routes of administration.

Cells are administered in a therapeutically effective dosage. Such a dosage is sufficient to generate significant numbers of new cardiomyocytes cells in the heart, and/or at least partially replace necrotic heart tissue, and/or produce a clinically significant change in heart function. A clinically significant improvement in heart performance can be determined by measuring the left ventricular ejection fraction, prior to, and after administration of cells, and determining at least a 5% increase, preferably 10% or more, in the total ejection fraction. Standard procedures are available to determine ejection fraction, as measured by blood ejected per beat. Dosages can vary from about $100-10^7$, $1000-10^6$ or $10^4-10^5$ cells.

Cells can be administered as pharmaceutical compositions, which can also include, depending on the formulation desired, pharmaceutically-acceptable, typically sterile, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Administration of stem cells of the present invention can be preceded, accompanied or followed by administration of growth factor(s) that stimulate proliferation and/or differentiation of the stem cells into cardiomyocytes. Growth factors can be administered intravenously or intraventricularly. Growth factors are administered in a dosage sufficient to cooperate with administered stem cells in generating significant numbers of new cardiomyocytes cells in the heart, and/or at least partially replace necrotic heart tissue, and/or produce a clinically significant change in heart function. Suitable growth factors include PDGF, EGF, FGF, NGF, EPO, IGF-1, IGF-2, G-CSF, IL-6 INF, Stem Cell Factor, and TNF-α.

In some embodiments, cardiac stem cells of the present invention are administered in combination with anti-inflammatory agents that arrest, reverse or partially ameliorate inflammation associated with heart disease. Suitable anti-inflammatory agents include antibodies to Mac-1, and L-, E and P-selectin. Cardiac stem cells of the present invention can also be administered with diuretics, ACE inhibitors and p-adrenergic blockers.

In some embodiments, the recipient patient of stem cells and the donor from which the cells are obtained are HLA-matched to reduce allotypic rejections. In some embodiments, the stem cells are isolated from a tissue or biopsy sample from a subject with heart disease and then subsequently reintroduced to treat the same subject. In other methods, cells are administered under cover of an immunosuppressive regime to reduce the risk of rejection Immunosuppressive agents that can be used include cyclosporin, corticosteroids, and OKT3. In other methods, immune responses are avoided by obtaining stem cells from the patient that is to be treated. Stem cells can be obtained by biopsy of heart tissue, and expanded in vitro before readministration. Alternatively, given the present provision of isolated cardiac stem cells, differentiation markers can be identified for these cells, and the cells can be isolated from the blood of the patient to be treated.

Cardiac Stem Cells in Drug Screening

The cardiac stem cells of the present invention can be used to test compounds for activity in promoting or inhibiting proliferation and/or differentiation of the cells. In general, a compound being tested is contacted with a population of cardiac stem cells, optionally, in the presence of other agents known to promote or inhibit the metabolic pathway or phenotype of interest, and phenotypic and metabolic changes are monitored in comparison with a control in which the compound being tested is absent.

Compounds to be tested include known or suspected growth factors, and analogs thereof, libraries of natural compounds not previously known to have activity in promoting proliferation or differentiation and combinatorial libraries of compounds. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Compounds that cause cardiac-derived stem cells to proliferate and/or differentiate into cardiomyocytes are useful as therapeutic agents in the same conditions as the cardiac stem cells are useful. Such compounds can be administered alone to stimulate proliferation and differentiation of endogenous cardiac stem cells, or can be administered in conjunction with exogenous cardiac stem cells. Such compounds are screened for proliferating activity by contacting them with cardiac stem cells in growth media, and monitoring an increase in cell count, or incorporation of 3H-thymidine. Compounds are screened for promoting differentiation to cardiomyocytes by monitoring cells with the characteristic morphological appearance and differentiation markers of cardiomyocytes.

Similarly, compounds can be monitored for activity in promoting differentiation of cardiac stem cells to other differentiated cell types, such as smooth muscle cells, skeletal muscle cells, osteoblasts and chondrocytes. Activity is detected by detecting the characteristic morphological appearance and differentiation markers of one of these cell types. Compounds with activity in promoting differentiation to one of the above cell types are useful in treating patients with degenerative diseases of bone, muscle or cartilage.

Compounds that inhibit differentiation of stem cells to certain cell types such as adipocytes can also be useful in some circumstances. For example, compounds that inhibit differentiation of stem cells to adipocytes can be used in treating obesity.

Such compounds are identified by contacting a compound under test with cardiac stem cells under conditions that would otherwise lead to differentiation of the stem cells to a certain cell type, and monitoring a decreased frequency or extent of conversion to the cell type relative to a control in which the compound is omitted.

Compounds identified as therapeutic agents by such screening with the stem cells of the present invention are formulated for therapeutic use as pharmaceutical compositions.

Kits

Another aspect of the invention encompasses kits for treating disease in a subject. A variety of kits having different components are contemplated by the current invention. In some embodiments, the kit will include stem cells of the present invention. In another embodiment, the kit will include means for collecting a biological sample, means for isolating stem cells from the biological sample, and instructions for use of the kit contents. In certain embodiments, the kit comprises a means for enriching or isolating stem cells in a biological sample. In further aspects, the means for enriching or isolating stem cells comprises reagents necessary to enrich or isolate stem cells from a biological sample. In certain aspects, the kit comprises a means for quantifying the amount of stem cells. In further aspects, the means for quantifying the amount of stem cells comprises reagents necessary to detect the amount of stem cells.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1

Isolation and Characterization of Cardiac Stem Cells

Cardiac stem cells were isolated from heart tissue as follows. Atrial tissue was obtained from 3 month old male Harlan Sprague Dawley rats. Atrial tissue was cut into 1- to 2-mm$^3$ pieces and digested with 0.2% trypsin (Life Technologies) and 0.1% collagenase IV (Life Technologies) for a total of 10 minutes. The remaining tissue fragments were cultured as "explants" in explant medium (CEM), which was composed of IMDM supplemented with 10% fetal bovine serum (FBS; Lonza), 100 U/mL, penicillin G, 100 μg/mL, streptomycin, and 2 mmol/L 1-glutamine (Sigma-Aldrich). After 21 days in culture, cardiac stem cells were collected by trypsinization. c-Kit positive cells were separated from the cell outgrowths using magnetic beads (MACS, Miltenyi Biotec) according to the manufacturer's protocol and analyzed by flow cytometry to validate the purity.

Total RNA was extracted from the cardiac stem cells using PureLink RNA Mini Kit (Life Technologies) according to the manufacturer's protocol. RNA was then quantified with a Quanti-iT RiboGreen RNA Assay Kit and assessed using a BioTek Synergy HT Microplate Reader (excitation/emission 480/520 nm). Total RNA (200 ng) was reverse-transcribed with a QuantiTect Reverse Transcription kit (Qiagen). Real-time RT-PCR was conducted using Rower SYBR Green Master Mix (Applied Biosystems) on a StepOnePlus Real-time PCR System (Applied Biosystems). Specific primers were synthesized by Life Technologies. CYPA was used as a reference gene. Data analysis was performed on StepOne software version 2.1 (Applied Biosystems) using the comparative Ct ($\Delta\Delta$Ct) quantitation method.

In another series of experiments, isolated cardiac stem cells were lysed in RIPA buffer (Thermo Scientific) containing Halt Phosphatase and Proteinase inhibitor cocktail (Thermo Scientific) according to the manufacturer's protocol. Protein concentration was determined using a BCA Protein Assay kit (Thermo Scientific). An equal amount of protein (50 μg) was loaded in each well of 4% to 12% bis-tris gels gel (Life Sciences) and subjected to electrophoresis. Proteins were transferred to a PVDF membrane (Millipore) and then blocked with 5% nonfat dry milk in Tris-buffered saline followed by overnight incubation with primary antibodies at 4° C. Antibodies against p-Smad2/3, Smad2/3 (Cell Signaling), and Nanog (Millipore) were used. Blots were probed with an anti-β-actin (Sigma Aldrich) antibody as a loading control. Membranes were washed in Tris-buffered saline containing 0.05% Tween 20. Corresponding horseradish peroxidase-conjugated anti-rabbit or anti-mouse IgG (Invitrogen) was used as secondary antibodies Immunoreactive proteins were detected by chemiluminescence (Thermo Scientific). Band intensity was determined using FluorChem 8900 software (Alpha Innotech Corp).

In another series of experiments, isolated cardiac stem cells were fixed in 70% ethanol and labeled with the following antibodies: c-Kit, Nanog, SMA, Vimentin, KDR, CD34, CD45, CD105, CD90, CD29, CD73, and Wt1. Cells were treated with secondary antibodies corresponding to either anti-rabbit or anti-mouse IgG conjugated with Alexa-488, phycoerythrin (PE) or PE-Cy5.5 (Invitrogen). For a negative control, cells were labeled with isotype IgG instead of primary antibody. Cell events were detected using FACS Calibur flow cytometer equipped with argon laser (BD Biosciences). Data was analyzed using CellQuest software (BD Biosciences).

Table 1 below shows characterization data for the cardiac stem cells isolated from atrial tissue. As shown in Table 1, the isolated cardiac stem cells expressed c-Kit, Nanog, Sox2, Hey1, SMA, Vimentin, Cyclin D2, Snail, E-cadherin, Nkx2.5, GATA4, MHCa, TnT, KDR, CD105, CD90, CD29, CD73, and Wt1. Cardiac stem cells did not express CD34 or CD45.

TABLE 1

| Marker | Expression | FACS % |
|---|---|---|
| c-Kit | 0.84 ± 0.37 | 87 ± 2.6 |
| Nanog | 0.87 ± 0.44 | 18.3 ± 6 |
| Sox2 | 1.7 ± 0.5 | No data |
| Hey1 | 1.7 ± 0.45 | No data |
| SMA | 873 ± 314 | 16.1 ± 6.7 |
| Vimentin | 2013 ± 131 | 40.4 ± 5.1 |
| Cyclin D2 | 1.65 ± 0.45 | No data |
| Snail | 35.9 ± 3.9 | No data |
| E-cadherin | 10 ± 3.2 | No data |
| Nkx2.5 | 1.2 ± 0.6 | No data |
| GATA4 | 13.9 ± 2.9 | No data |
| MHCa | 0.18 ± 0.08 | No data |
| TnT | 0.65 ± 0.2 | No data |
| KDR | 4.1 ± 1.9 | 15 ± 1.2 |
| CD34 | No data | <1 |
| CD45 | No data | <1 |
| CD105 | No data | 69 ± 4.3 |
| CD90 | No data | 37 ± 3.4 |
| CD29 | No data | 34 ± 1 |
| CD73 | No data | 49 ± 2.7 |
| Wt1 | No data | 26 ± 3.4 |

Expression levels normalized to β-actin, fold changes were calculated as a ratio of expression in c-Kit negative group to expression in c-Kit positive group.

These results showed that cardiac stem cells of the present invention express c-Kit, Nanog, Sox2, Hey1, SMA, Vimentin, Cyclin D2, Snail, E-cadherin, Nkx2.5, GATA4, MHCa, TnT, KDR, CD105, CD90, CD29, CD73, and Wt1 but not CD34 or CD45. These results demonstrated that cardiac stems of the present invention may be isolated and characterized by differential RNA expression. The results further showed that methods of the present invention are useful for isolating cardiac stem cells and for selective enrichment of cardiac stem cells. These results further indicated that the methods and cells of the present invention would be useful for treating a subject suffering from a cardiac disease.

In another series of experiments, cardiac stem cells were isolated from rats that had developed chronic heart failure (CHF) six weeks after myocardial infarction. In these studies, two-month-old Sprague Dawley rats (Harlan Laboratories) were anesthetized and ventilated. Following a left thoracotomy, the heart was expressed, and the left anterior descending coronary artery was ligated using a 5-0 TiCron suture. The lungs were briefly hyperinflated, the chest was closed using 2-0 silk, and the rodents were allowed to recover with a pain management regiment of buprenorphine.

Hemodynamic statistics were collected from the rats six weeks post-MI using a pressure-volume catheter (Millar Instruments) inserted into the right carotid artery and advanced into the left ventricle. The animals were systemically anesthetized with Inactin (125 mg/kg) and intubated, and the steady-state measurements were collected prior to ventilation. The data were analyzed using PVAN 3.6. software (Millar Instruments).

CHF animals were selected on the basis of left ventricle end-diastolic pressure measurement ≥20 mm Hg and scar size ≥30% of left ventricle. Approximately 35% of infarcted animals were classified as CHF and utilized in subsequent experiments; non-CHF animals were excluded from the study. Atrial tissues were collected six weeks after MI from CHF (n=10) animals. Cardiac stem cells were isolated from atrial tissues as described above. Additionally, total RNA and proteins were extracted from the cardiac stem cells as described above.

Table 2 below shows characterization data for the cardiac stem cells isolated from CHF atrial tissue. As shown in Table 2, the isolated cardiac stem cells expressed c-Kit, Nanog, Sox2, Hey1, SMA, Vimentin, Cyclin D2, Snail, and E-cadherin.

TABLE 2

| Marker | CHF Expression vs. shams, fold changes |
|---|---|
| c-Kit | 0.4 |
| Nanog | 0.5 |
| Sox2 | 0.2 |
| Hey1 | 0.17 |
| SMA | 1.6 |
| Vimentin | 1.8 |
| Cyclin D2 | 0.7 |
| Snail | 2.5 |
| E-cadherin | 0.3 |

Expression levels normalized to β-actin, fold changes were calculated as a ratio of expression in c-Kit negative group to expression in c-Kit positive group.

These results showed that cardiac stem cells of the present invention express c-Kit, Nanog, Sox2, Hey1, SMA, Vimentin, Cyclin D2, Snail, and E-cadherin. These results demonstrated that cardiac stems of the present invention may be isolated and characterized by differential RNA expression. The results further showed that methods of the present invention are useful for isolating cardiac stem cells and for selective enrichment of cardiac stem cells. These results further indicated that the methods and cells of the present invention would be useful for treating a subject suffering from a cardiac disease.

Example 2

Cardiac Differentiation Potential of c-Kit Positive Cells In Vitro

The differentiation potential of c-Kit+ cardiac stem cells was examined as follows. Cardiac stem cells were isolated from heart tissue as described in Example 1 above. Cells were subsequently cultured in cardiac differentiation medium (EMD Millipore) supplemented with 2 μmol/L Mocetinostat (SelleckChem) for 7 days. Expression of cardiac troponin T (TnT) was evaluated by immunocytochemistry. TnT is an accepted marker for cardiac differentiation. Cells were fixed/permeabilized with a 1:1 acetone:ethanol mixture, blocked with 3% BSA in PBS, and labeled with mouse anti-TnT primary antibody (Abcam). Specific staining was visualized using anti-mouse secondary antibodies conjugated with Alexa 568 (Molecular Probes). Nuclei were stained with 4',6-diamidino-2-phenylindole (Invitrogen). TnT-positive cells were quantified in 5 random microscopic fields. The percentage of TnT-positive cells was calculated as the number of positively stained cells normalized to the total number of cells.

Immunohistochemistry analysis showed that 11.7% of isolated cardiac stem cells were TnT-positive. These results showed that cardiac stem cells of the present invention can differentiate into cardiac cells in vitro. The results further indicated that the methods and cells of the present invention would be useful for treating a subject suffering from a cardiac disease.

In another series of experiments, the differentiation potential of c-Kit+ cardiac stem cells from CHF animals was examined as follows. Myocardial infarction was induced in two-month-old Sprague Dawley rats (Harlan Laboratories) as described above in Example 1. Six weeks after MI and after hemodynamic confirmation of the development of CHF in the animals, cardiac stem cells were isolated from CHF heart tissue as described above in Example 1. Cells were subsequently cultured in cardiac differentiation medium (EMD Millipore) supplemented with 2 µmol/L Mocetinostat (SelleckChem) for 7 days. Expression of cardiac troponin T (TnT) was evaluated by immunocytochemistry. TnT is an accepted marker for cardiac differentiation. Cells were fixed/permeabilized with a 1:1 acetone:ethanol mixture, blocked with 3% BSA in PBS, and labeled with Mouse anti-TnT primary antibody (Abcam). Specific staining was visualized using anti-mouse secondary antibodies conjugated with Alexa 568 (Molecular Probes). Nuclei were stained with 4',6-diamidino-2-phenylindole (Invitrogen). TnT-positive cells were quantified in 5 random microscopic fields. The percentage of TnT-positive cells was calculated as the number of positively stained cells normalized to the total number of cells.

Immunohistochemistry analysis showed that 8.0% of isolated cardiac stem cells were TnT-positive. These results showed that cardiac stem cells of the present invention can differentiate into cardiac cells in vitro. The results further indicated that the methods and cells of the present invention would be useful for treating a subject suffering from a cardiac disease.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A composition comprising: one or more isolated cardiac stem cells derived from non-embryonic tissue, wherein said cardiac stem cells express c-Kit, Nanog, Wt1 and Sox2 but not CD34 or CD45.

2. The composition of claim 1, wherein the tissue is human tissue.

3. The composition of claim 1, wherein the cardiac stem cells are human cardiac stem cells.

4. The composition of claim 1, wherein the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, and CD73.

5. The composition of claim 1, wherein the tissue is obtained from a subject having or suspected of having a cardiac disease.

6. A method for the isolation of cardiac stem cells, comprising the selective enrichment of cardiac stem cells which express c-Kit, Nanog, Wt1 and Sox2 but not CD34 or CD45.

7. The method of claim 6, further comprising dissociating a source of cardiac stem cells from a cardiac tissue sample; and identifying a cardiac stem cell expressing c-Kit, Nanog, Wt1 and Sox2.

8. The method of claim 6, further comprising centrifuging a suspension of cells from heart tissue of a subject on a density gradient; isolating a layer of cells comprising cardiac stem cells; culturing the isolated cells until a population of cardiac stem cells is detectable.

9. The method of claim 6, further comprising obtaining heart tissue from a subject; digesting the heart tissue with collagenase.

10. The method of claim 6, further comprising obtaining heart tissue from a subject having or suspected of having a cardiac disease.

11. The method of claim 6, wherein the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, and CD73.

12. A method of treating a subject suffering from heart disease, comprising administering to the subject an effective dose of cardiac stem cells, wherein the cardiac stem cells express c-Kit, Nanog, Wt1 and Sox2 but not CD34 or CD45.

13. The method of claim 12, whereby the cardiac stem cells proliferate and differentiate to produce cardiomyocytes.

14. The method of claim 12, wherein the subject has a heart disease selected from the group consisting of chronic heart failure, myocardial infarction, congestive heart failure, congenital heart disease, cardiomyopathy, pericarditis, angina, and coronary artery disease.

15. The method of claim 12, further comprising administering an agent to the subject.

16. The method of claim 15, wherein the agent is selected from the group consisting of an ACE inhibitor, an aldosterone inhibitor, an angiotensin II receptor blocker, a beta-blocker, a calcium channel blocker, a statin, digoxin, a diuretic, a vasodilator, and an anticoagulant.

17. The method of claim 12, further comprising administering an agent to the cardiac stem cells prior to administering the cardiac stem cells to the subject.

18. The method of claim 17, wherein the agent is selected from the group consisting of PDGF, EGF, FGF, NGF, EPO, IGF-1, IGF-2, G-CSF, IL-6 INF, Stem Cell Factor, and TNF-α.

19. The method of claim 12, wherein the cardiac stem cells further express one or more markers selected from the group consisting of Hey1, SMA, Vimentin, Cyclin D2, Snail, E-cadherin, Nkx2.5, GATA4, MHCa, TnT, KDR, CD105, CD90, CD29, and CD73.

* * * * *